US009486404B2

(12) United States Patent
Burdick et al.

(10) Patent No.: US 9,486,404 B2
(45) Date of Patent: Nov. 8, 2016

(54) INFARCTION TREATMENT COMPOSITIONS AND METHODS

(75) Inventors: Jason A. Burdick, Philadelphia, PA (US); Robert C. Gorman, Lower Gwynedd, PA (US); Joseph H. Gorman, III, Lower Gwynedd, PA (US); Jamie L. Ifkovits, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 69 days.

(21) Appl. No.: 13/430,872

(22) Filed: Mar. 27, 2012

(65) Prior Publication Data

US 2012/0251483 A1    Oct. 4, 2012

Related U.S. Application Data

(60) Provisional application No. 61/468,140, filed on Mar. 28, 2011.

(51) Int. Cl.

| | | |
|---|---|---|
| *A61K 31/785* | (2006.01) | |
| *A61K 31/728* | (2006.01) | |
| *A61K 31/25* | (2006.01) | |
| *A61K 31/722* | (2006.01) | |
| *A61K 31/717* | (2006.01) | |
| *A61K 31/734* | (2006.01) | |
| *A61K 31/727* | (2006.01) | |
| *A61K 35/12* | (2015.01) | |
| *A61K 35/14* | (2015.01) | |
| *A61K 38/18* | (2006.01) | |
| *A61K 9/10* | (2006.01) | |
| *A61K 9/00* | (2006.01) | |
| *A61K 45/06* | (2006.01) | |
| *A61K 47/32* | (2006.01) | |
| *A61K 38/00* | (2006.01) | |

(52) U.S. Cl.
CPC ............. *A61K 9/0024* (2013.01); *A61K 31/25* (2013.01); *A61K 31/717* (2013.01); *A61K 31/722* (2013.01); *A61K 31/727* (2013.01); *A61K 31/728* (2013.01); *A61K 31/734* (2013.01); *A61K 31/785* (2013.01); *A61K 45/06* (2013.01); *A61K 47/32* (2013.01); *A61K 38/00* (2013.01)

(58) Field of Classification Search
USPC ......................................................... 424/450
See application file for complete search history.

(56) References Cited

U.S. PATENT DOCUMENTS

| | | | |
|---|---|---|---|
| 4,699,784 A | 10/1987 | Shih et al. | |
| 5,834,029 A | 11/1998 | Bellamkonda et al. | |
| 7,220,270 B2 | 5/2007 | Sawhney et al. | |
| 2004/0028745 A1 | 2/2004 | Bouhadir et al. | |
| 2004/0241241 A1* | 12/2004 | Lopatin | 424/486 |
| 2005/0271631 A1* | 12/2005 | Lee et al. | 424/93.7 |
| 2006/0173088 A1 | 8/2006 | Nozaki et al. | |
| 2006/0229492 A1* | 10/2006 | Gelfand et al. | 600/37 |
| 2007/0059248 A1 | 3/2007 | Unger et al. | |
| 2007/0122392 A1 | 5/2007 | Gerecht-Nir et al. | |
| 2007/0185008 A1 | 8/2007 | Hennink et al. | |
| 2007/0190018 A1 | 8/2007 | Papisov | |
| 2007/0233219 A1* | 10/2007 | Shafi et al. | 623/1.1 |
| 2008/0065048 A1* | 3/2008 | Sabbah et al. | 604/511 |
| 2008/0279944 A1 | 11/2008 | Sawhney | |
| 2009/0238875 A1* | 9/2009 | Noh et al. | 424/487 |
| 2010/0261196 A1* | 10/2010 | Evans et al. | 435/7.1 |
| 2012/0114615 A1 | 5/2012 | Burdick et al. | |

FOREIGN PATENT DOCUMENTS

WO    WO 2010/074958    7/2010

OTHER PUBLICATIONS

Ifkovits JL, Injectable hydrogel properties influence infarct expansion and extent of postinfarction left ventricular remodeling in an ovine model, PNAS, 2010, 107, 25, 11507-11512.*
Bitter et al., "A Modified Uronic Acid Carbazole Reaction," Analytical Biochemistry, Oct. 1962, 4(4), 330-334.
Blom et al., "Infarct size reduction and attenuation of global left ventricular remodeling with the CorCap cardiac support device following acute myocardial infarction in sheep," Heart Fail Rev., Jun. 2005, 10(2), 125-139.
Burdick et al., "Controlled degradation and mechanical behavior of photopolymerized hyaluronic acid networks," Biomacromolecules, Jan.-Feb. 2005, 6(1), 386-391.
Christman et al., "Fibrin glue alone and skeletal myoblasts in a fibrin scaffold preserve cardiac function after myocardial infarction," Tissue Engineering, Mar.-Apr. 2004, 10(3-4), 403-409.
Christman et al., "Injectable fibrin scaffold improves cell transplant survival, reduces infarct expansion, and induces neovasculature formation in ischemic myocardium," Journal of the American College of Cardiology, Aug. 2004, 44(3), 654-660.
Dai et al., "Thickening of the infarcted wall by collagen injection improves left ventricular function in rats," Journal of the American College of Cardiology, Aug. 2005, 46(4), 714-719.
Davis et al., "Local myocardial insulin-like growth factor 1 (IGF-1) delivery with biotinylated peptide nanofibers improves cell therapy for myocardial infarction," Proceedings of the National Academy of Sciences of the United States of America, May 2006, 103(21), 8155-8160.
Dobner et al., "A Synthetic Non-degradable Polyethylene Glycol Hydrogel Retards Adverse Post-infarct Left Ventricular Remodeling," Journal of Cardiac Failure, Sep. 2009, 15(7), 629-636.
Eaton et al., "Regional Cardiac Dilatation after Acute Myocardial-Infarction—Recognition by 2-Dimensional Echocardiography," New England Journal of Medicine, Jan. 1979, 300(2), 57-62.

(Continued)

*Primary Examiner* — Frederick Krass
*Assistant Examiner* — Celeste A Roney
(74) *Attorney, Agent, or Firm* — Baker & Hostetler LLP

(57) ABSTRACT

Provided are methods of treating cardiac infarction by using an injectable material to influence cardiac structure and remodeling after infarction. Also provided are kits that comprise an injectable material to influence cardiac structure.

19 Claims, 14 Drawing Sheets

(56) References Cited

OTHER PUBLICATIONS

Enomoto et al., "Early ventricular restraint after myocardial infarction: Extent of the wrap determines the outcome of remodeling," Annals of Thoracic Surgery, Mar. 2005, 79(3), 881-887.
Epstein et al., "MR tagging early after myocardial infarction in mice demonstrates contractile dysfunction in adjacent and remote regions," Magnetic Resonance in Medicine, Aug. 2002, 48(2), 399-403.
Erlebacher et al., "Early Dilation of the Infarcted Segment in Acute Transmural Myocardial-Infarction—Role of Infarct Expansion in Acute Left-Ventricular Enlargement", Journal of the American College of Cardiology, Aug. 1984, 4(2), 201-208.
Fujimoto et al., "Synthesis, characterization and therapeutic efficacy of a biodegradable, thermoresponsive hydrogel designed for application in chronic infarcted myocardium," Biomaterials, Sep. 2009, 30(26), 4357-4368.
Gheorghiade et al., "Chronic heart failure in the United States: A manifestation of coronary artery disease," Circulation, Jan. 1998, 97(3), 282-289.
Gorman et al., "The potential role of ventricular compressive therapy," Surgical Clinics of North America, Feb. 2004, 84(1), 45-59.
Hochman et al., "Limitation of Myocardial Infarct Expansion by Reperfusion Independent of Myocardial Salvage," Circulation, Jan. 1987, 75(1), 299-306.
International Patent Application No. PCT/US2009/067141: International Search Report and Written Opinion dated Feb. 5, 2010, 12 pages.
Jackson et al., "Border zone geometry increases wall stress after myocardial infarction: contrast echocardiographic assessment," American Journal of Physiology—Heart and Circulatory Physiology. Feb. 2003, 284(2), H475-H479.
Jackson et al., "Extension of borderzone myocardium in postinfarction dilated cardiomyopathy," Journal of the American College of Cardiology, Sep. 2002, 40(6), 1160-1167.
Jneid et al., "Impact of time of presentation on the care and outcomes of acute myocardial infarction," Circulation, May 2008, 117(19), 2502-2509.
Kelley et al., "Restraining infarct expansion preserves left ventricular geometry and function after acute anteroapical infarction," Circulation, Jan. 1999, 99(1), 135-142.
Kloner et al., "New insights into the open artery hypothesis," Circulation Research, Jul. 2008, 103(1), 1-3.
Kofidis et al., "Novel injectable bioartificial tissue facilitates targeted, less invasive, large-scale tissue restoration on the beating heart after myocardial injury," Circulation, Aug. 2005, 112(9 Suppl.), I-173-I-177.
Kramer et al., "Regional Differences in Function within Noninfarcted Myocardium during Left-Ventricular Remodeling," Circulation, Sep. 1993, 88(3), 1279-1288.
Landa et al., "Effect of injectable alginate implant on cardiac remodeling and function after recent and old infarcts in rat," Circulation, Mar. 2008, 117(11), 1388-1396.
Leor et al., "A novel injectable alginate scaffold promotes angiogenesis and preserves left ventricular geometry and function after extensive myocardial infarction in rat," Circulation, Oct. 2004, Abstract #1334, 110(17) Suppl., 111-279.
Leor et al., "Intracoronary Injection of In Situ Forming Alginate Hydrogel Reverses Left Ventricular Remodeling After Myocardial Infarction in Swine," Journal of the American College of Cardiology, Sep. 2009, 54(11), 1014-1023.
Lima et al., "Impaired Thickening of Nonischemic Myocardium during Acute Regional Ischemia in the Dog," Circulation, May 1985, 71(5), 1048-1059.
Mann D. L., "Mechanisms and models in heart failure: A combinatorial approach," Circulation, Aug. 1999, 100(9), 999-1008.
Markovitz et al., "Large Animal-Model of Left-Ventricular Aneurysm," Annals of Thoracic Surgery, Dec. 1989, 48(6), 838-845.
Miura et al., "Limitation of myocardial infarct size in the clinical setting: current status and challenges in translating animal experiments into clinical therapy," Basic Res. Cardiol., Nov. 2008, 103(6), 501-513.
Moainie et al., "Infarct restraint attenuates remodeling and reduces chronic ischemic mitral regurgitation after postero-lateral infarction," Annals of Thoracic Surgery, Aug. 2002, 74(2), 444-449.
Mukherjee et al., "Targeted myocardial microinjections of a biocomposite material reduces infarct expansion in pigs," Annals of Thoracic Surgery, Oct. 2008, 86(4), 1268-1276.
Opie L. H., "Ventricular Function. Essential Cardiology: Principles and Practice," ed. Rosendorff C., Humana Press, Totowa, 2Ed., 2005, pp. 37-54.
Pilla et al., "Early postinfarction ventricular restraint improves borderzone wall thickening dynamics during remodeling," Ann. Thorac. Surg., Dec. 2005, 80(6), 2257-2262.
Pilla et al., "Theoretic impact of infarct compliance on left ventricular function," Ann. Thorac. Surg., Mar. 2009, 87(3), 803-810.
Ryan, et al., "Dermal Filler Injection: A Novel Approach for Limiting Infarct Expansion," Annals of Thoracic Surgery, Jan. 2009, 87(1), 148-155.
Singelyn et al., "Naturally derived myocardial matrix as an injectable scaffold for cardiac tissue engineering," Biomaterials, Oct. 2009, 30(29), 5409-5416.
Wall et al., "Theoretical impact of the injection of material into the myocardium: A finite element model simulation," Circulation, Dec. 2006, 114(24), 2627-2635.
Weisman et al., "Myocardial Infarct Expansion, Infarct Extension, and Reinfarction-Pathophysiologic Concepts," Progress in Cardiovascular Diseases, Sep.-Oct. 1987, 30(2), 73-110.
Yu et al., "Restoration of left ventricular geometry and improvement of left ventricular function in a rodent model of chronic ischemic cardiomyopathy," Journal of Thoracic and Cardiovascular Surgery, Jan. 2009, 137(1), 180-187.

* cited by examiner

FIG. 13

| Metric | Control Infarct | MeHA High | MeHA Low |
|---|---|---|---|
| n | 9 | 6 | 5 |
| Weight (kg) | 40.6 ± 0.7 | 40.8 ± 0.7 | 39.4 ± 1.3 |
| Infarct Area | 28.64 ± 1.0 | 23.87 ± 0.93[a] | 26.42 ± 1.56 |
| Infarct Length | | | |
| Post-MI | 7.41 ± 0.23 | 7.37 ± 0.16 | 7.34 ± 0.10 |
| 2 week | 8.28 ± 0.39 | 8.04 ± 0.12 | 8.26 ± 0.14 |
| 8 week | 8.91 ± 0.55 | 8.47 ± 0.16 | 8.98 ± 0.15 |
| NEDV | | | |
| Post-MI | 1.30 ± 0.08 | 1.32 ± 0.08 | 1.50 ± 0.13 |
| 2 week | 1.76 ± 0.22 | 1.63 ± 0.12 | 1.80 ± 0.23 |
| 8 week | 2.06 ± 0.20 | 1.70 ± 0.13 | 2.08 ± 0.25 |
| DoB 2.5 | 1.41 ± 0.15 | 1.22 ± 0.07 | 1.58 ± 0.29 |
| DoB 5.0 | 1.19 ± 0.13 | 0.90 ± 0.07 | 1.20 ± 0.28 |
| NESV | | | |
| Post-MI | 1.38 ± 0.08 | 1.45 ± 0.08 | 1.66 ± 0.18 |
| 2 week | 2.10 ± 0.30 | 1.90 ± 0.12 | 2.22 ± 0.40 |
| 8 week | 2.43 ± 0.29 | 2.00 ± 0.16 | 2.52 ± 0.38 |
| DoB 2.5 | 1.64 ± 0.21 | 1.32 ± 0.10 | 1.88 ± 0.44 |
| DoB 5.0 | 1.38 ± 0.18 | 0.95 ± 0.10 | 1.50 ± 0.43 |
| EDV | | | |
| Baseline | 51.64 ± 2.27 | 56.97 ± 2.92 | 51.40 ± 2.37 |
| Post-MI | 65.94 ± 2.30 | 71.73 ± 3.81 | 72.26 ± 2.88 |
| 2 week | 88.08 ± 7.99[b] | 91.23 ± 5.22[b] | 91.60 ± 9.39[b] |
| 8 week | 103.44 ± 8.10[b] | 95.78 ± 6.50[b] | 106.08 ± 8.84[b] |
| DoB 2.5 | 71.53 ± 7.63 | 69.75 ± 5.64 | 79.5 ± 11.68 |
| DoB 5.0 | 60.46 ± 6.29 | 51.48 ± 3.73 | 60.26 ± 10.97 |
| ESV | | | |
| Baseline | 31.69 ± 1.90 | 34.17 ± 1.58 | 30.20 ± 1.36 |
| Post-MI | 42.67 ± 2.12 | 47.42 ± 2.64 | 46.50 ± 2.65 |
| 2 week | 63.38 ± 6.67[b] | 64.22 ± 3.77[b] | 65.94 ± 9.98[b] |
| 8 week | 74.03 ± 6.38[b] | 67.18 ± 4.64[b] | 75.32 ± 8.72[b] |
| DoB 2.5 | 50.87 ± 6.12 | 44.98 ± 3.80 | 55.82 ± 11.00 |
| DoB 5.0 | 42.07 ± 5.20 | 33.13 ± 3.17 | 43.64 ± 11.24 |

FIG. 13 (continued)

| | | | |
|---|---|---|---|
| *Cardiac Output* | | | |
| Baseline | 4.27 ± 0.24 | 3.82 ± 0.31 | 4.32 ± 0.26 |
| 2 week | 3.06 ± 0.13[b] | 3.18 ± 0.26 | 3.30 ± 0.33 |
| 8 week | 3.04 ± 0.35[b] | 3.28 ± 0.18 | 4.18 ± 0.75 |
| DoB 2.5 | 4.51 ± 0.45 | 4.38 ± 0.35 | 5.02 ± 1.08 |
| DoB 5.0 | 4.92 ± 0.61 | 5.15 ± 0.42 | 5.14 ± 0.62 |
| *Ejection Fraction* | | | |
| Baseline | 38.89 ± 1.81 | 40.00 ± 1.16 | 41.22 ± 0.94 |
| Post-MI | 35.47 ± 1.62 | 33.80 ± 1.69 | 35.76 ± 1.67 |
| 2 week | 28.39 ± 1.41[b] | 29.40 ± 0.95[b] | 29.18 ± 3.37[b] |
| 8 week | 28.65 ± 0.99[b] | 29.67 ± 1.21[b] | 29.60 ± 2.67[b] |
| DoB 2.5 | 29.54 ± 1.09 | 35.33 ± 1.97 | 31.20 ± 2.76 |
| DoB 5.0 | 31.23 ± 1.29 | 35.97 ± 2.00 | 30.26 ± 4.31 |

INFARCTION TREATMENT COMPOSITIONS AND METHODS

CROSS REFERENCE TO RELATED APPLICATION

The present application claims priority to U.S. Application No. 61/468,140, "Infarction Treatment Compositions and Methods," filed on Mar. 28, 2011, which application is incorporated herein by reference in its entirety for any and all purposes.

GOVERNMENT RIGHTS

This invention was made with government support under grants HL63954, HL73021, and HL76560, awarded by the National Institutes of Health. The government has certain rights in this invention.

TECHNICAL FIELD

The present invention relates to the field of cardiac treatment and to the field of polymeric materials.

BACKGROUND

Left ventricular (LV) remodeling caused by a myocardial infarction (MI) is responsible for almost 70% of the 5 million cases of heart failure that have occurred in the United States in recent years. Early infarct expansion or stretching has been associated with poor long-term prognosis and has been identified as the mechanical phenomenon that initiates and sustains the process of adverse post-MI LV remodeling that leads to heart failure.

Infarct expansion causes abnormal stress distribution in myocardial regions outside the infarction, especially in the adjacent borderzone (BZ) region, which stress distribution puts this region at a mechanical disadvantage. With time increased regional stress is the impetus for several maladaptive biologic processes, such as myocyte apoptosis and matrix metalloproteinase activation that inherently alter the contractile properties of normally perfused myocardium. Once initiated, these maladaptive processes lead to a heart failure phenotype difficult to reverse by medical or surgical means.

SUMMARY

First provided are methods of treating a subject. These methods include delivering a monomer to cardiac tissue comprising an infarction; and polymerizing at least a portion of the monomer to form a reinforced region of the cardiac tissue.

Also provided are kits. The kits suitably include an injector adapted to deliver fluid to cardiac tissue; and a quantity of polymerizable material, the polymerizable material being selected for delivery to cardiac tissue.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 13 provides a table illustrating the in vivo effects of MeHA treatment on infarct size, geometry, and function. Data is plotted as the mean±standard error of the mean, $^a$ denotes $p<0.01$ compared to control infarct, $^b$ denotes $p<0.05$ compared to respective baseline value.

DETAILED DESCRIPTION OF ILLUSTRATIVE EMBODIMENTS

Figure 1:
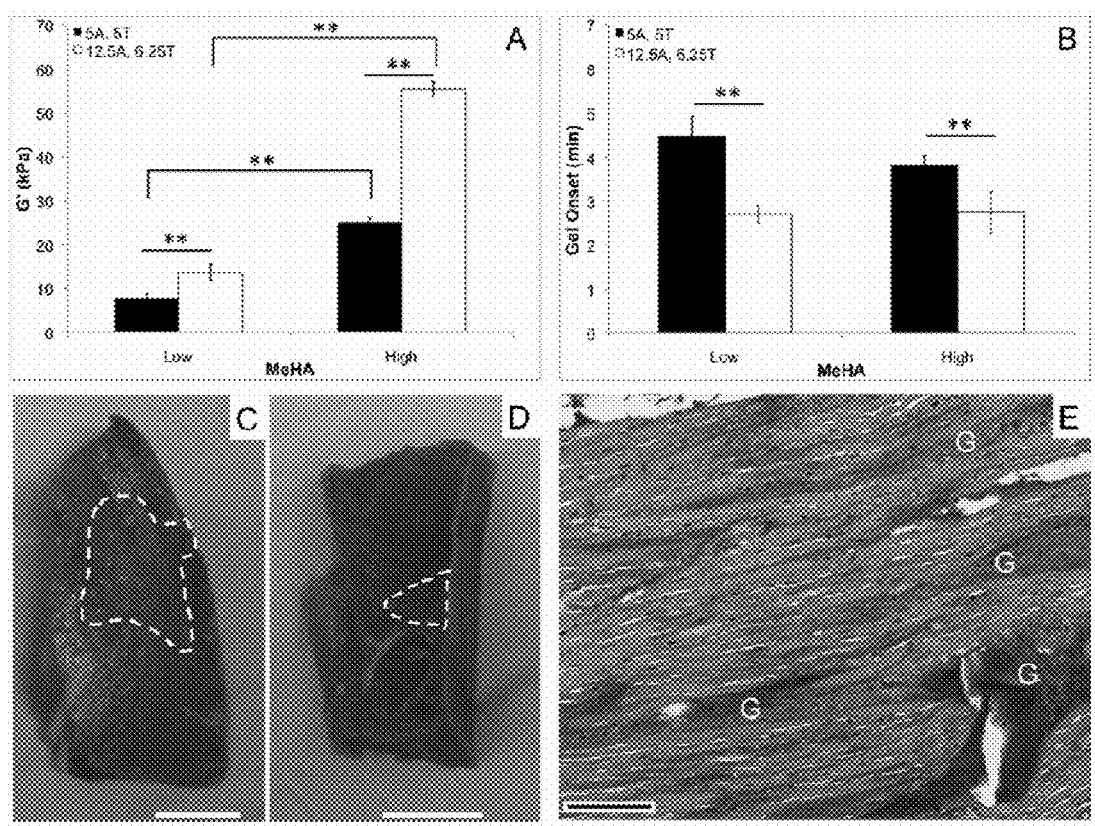
FIGS. 1A-1E adress hydrogel mechanical properties and gelation time behavior. Storage modulus (FIG. 1A) and gelation onset time (FIG. 1B) for various macromer (MeHA Low or High) and initiator (5.0 mM/5.0 mM or 12.5 mM/6.25 mM APS (A)/TEMED(T)) combinations. N=3 per group, data presented as mean±standard deviation, and ** denotes p<0.01. Explanted tissue with 4 wt % MeHA High (outlined with dashed line) gelled with either 5.0 mM APS/5.0 mM TEMED (FIG. 1C) or 12.5 mM APS/6.25 mM TEMED (FIG. 1D), showing differences in gel distribution based on initiator concentrations, scale bar=10 mm. Representative hematoxylin and eosin stained image of the cardiac tissue at the apex of a MeHA High gel (labeled with G) treated infarct 24 hours post-injection, demonstrating integration with tissue (FIG. 1E), scale bar=100 µm.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Any documents mentioned herein (including any and all documents mentioned in U.S. Application No. 61/468,140) are incorporated herein in their entireties for any and all purposes.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

In a first embodiment, the present disclosure provides methods of treating a subject suffering from an infarction or other cardiac ailment. The methods include delivering a monomer to cardiac tissue comprising an infarction and polymerizing at least a portion of the monomer to form a reinforced region that reinforces the cardiac tissue adjacent to or even within the infarcted region.

The methods are suitably applied to virtually any region of the heart that may suffer an infarction. Myocardial wall tissue is considered a particularly suitable material for application of the disclosed methods.

The monomer is suitably delivered to the interior of the tissue being treated. This may be accomplished by injecting the monomer. Injection may be accomplished with a syringe, a catheter, a pump, and the like.

Introduction of the monomer to the interior of the tissue may be accomplished by inserting a needle or other conduit into the tissue and then injecting the material. The introduction of the monomer is performed such that the monomer is integrated within the cardiac tissue being treated. An imaging device—such as an ultrasound machine or 3D electrocardiograph—may be used to assist in positioning and aiming an injection device so as to deliver the monomer to the desired location. Monomer may be delivered to a single location or multiple locations in the heart, depending on the user's needs.

In some embodiments, the user may introduce monomer to the exterior of the tissue being treated. The material may be applied (e.g., via injection) to a surface of the tissue being treated and then the user may allow the material to diffuse into the tissue. This may also be accomplished by syringes and catheters. The material may also be sprayed, dripped, pipetted, or otherwise applied to the surface of the tissue.

One may suitably locate the infarction within the cardiac tissue so as to assist with placement of the monomer material. A variety of techniques exist for locating infarctions, including ultrasound, x-rays, MRI, electrocardiogram, and the like. Identifying the location—or likely location—of an infarction before delivering the monomer material may enhance the effectiveness of the disclosed methods, although such identification is not required. The monomer may be placed in or on the infarcted area. The monomer may also be placed adjacent or near to the infarcted area, or may even be placed at a distance from the infarcted area.

The user may locate the infarction within the left ventricle, the right ventricle, the left atrium, the right atrium, the aorta, or other cardiac region. The infarction may be located via, e.g., fluoroscopy and cardiac catheterization. The user may locate an infracted area of the heart or weakened area of the heart that causes a heart valve (e.g., mitral valve, tricuspid valve).

A user may locate (or estimate the location of) an infarction and deliver monomer at essentially the same time. In this way, the user may locate and treat an infarction in a single procedure. Alternatively, one may locate the infarction before delivering the monomer, and the user may then use that existing location information to place the monomer during the injection procedure. A user may also use an imaging technique to determine the location of delivered monomer; in this way, the user may determine whether monomer was delivered to the desired location. The user may then elect to deliver additional monomer if desired.

A variety of monomers are considered suitable for the described methods. Monomers or macromers that polymerize to form biocompatible materials (e.g., hydrogels) are considered especially suitable. A non-exclusive listing of suitable monomers/macromers includes methacrylated hyaluronic acid, methacrylated/acrylated poly(ethylene glycol), acrylated poly(ethylene glycol), methacrylated/acrylated poly(vinyl alcohol), methacrylated/acrylated chitosan, methacrylated/acrylated cellulose, poly(n-isopropryl acrylamide), methacrylated/acrylated alginate, methacylated/acrylated heparin, and the like. Maleimides may be used to substitute for acrylates and methacrylates.

The reinforced region developed in the cardiac tissue may be a hydrogel; hydrogel materials are featured in some of the examples appended hereto. The reinforced region may also include an elastomer. Exemplary elastomers include Natural polyisoprene, synthetic polyisoprene, polybutadiene, chloroprene rubber (CR), polychloroprene, Neoprene, Baypren, and the like. Butyl rubber, halogenated butyl rubbers (chloro butyl rubber: CIIR; bromo butyl rubber: BIIR), styrene-butadiene Rubber (copolymer of styrene and butadiene, SBR), nitrile rubber (copolymer of butadiene and acrylonitrile, NBR), and hydrogenated Nitrile Rubbers (HNBR) Therban and Zetpol. C-Flex™ and silicone rubbers are also considered suitable elastomers.

As described above, materials that form crosslinked hydrogels are considered especially suitable, so reactive and hydrophilic macromers/monomers are useful in the disclosed methods. A material introduced to cardiac tissue may include one, two, or more different monomers so as to give rise to homopolymers or copolymer materials following polymerization and crosslinking. The monomer is suitably delivered with an initiator, a cross-linker, or both. For example, in the illustrative MeHA systems discussed herein, one may employ an initiator of APS (ammonium persulfate) and TEMED (tetramethylethylenediamine), together with methacrylated hyaluronic acid macromer.

The monomer suitably polymerizes, cross-links, or both at the desired tissue location. In some embodiments, the user may apply UV light or other initiator to the monomer composition to cure the composition. In the case of UV light, the user may apply the UV light by way of an appropriate lamp or instrument inserted into the subject so as to irradiate the monomer and effect polymerization or crosslinking.

The polymer of the reinforced region suitably differs in at least one mechanical property from cardiac tissue that has suffered an infarction. This mechanical property may be compressive modulus, elastic modulus, or both. The polymer suitably maintains the thickness of the cardiac tissue, by preventing thinning of the infarct region or even by thickening the infarct region. The reinforced region suitably has at least one mechanical property that is greater than the corresponding property of native cardiac tissue. The reinforced region suitably has at least one mechanical property that is about 2, 3, 5, 7, or even about 10 times greater than the corresponding property of native cardiac tissue. For example, the reinforced region may have a compressive modulus that is 110%, 150%, 300%, 500%, 700%, or even 1,000% the compressive modulus of native cardiac tissue. Likewise, the reinforced region may have an elastic modulus that is 110%, 150%, 300%, 500%, 700%, or even 1,000% the elastic modulus of native cardiac tissue.

It should be understood that the present disclosure is not limited to methods that create a single reinforced region of cardiac tissue. The disclosed methods, materials, and kits may create multiple reinforced regions of cardiac tissue. For example the disclosed methods may be used to reinforce multiple infarcted regions in a subject, or to provide multiple reinforced regions within an infarcted region. The reinforced regions may be of virtually any shape; they may be circular, oblong, polygonal, or linear, or combinations of these. Reinforced regions may be separate from one another, or may be connected by a region or zone of reinforcing polymer material. The reinforced region may also be of virtually any size. For example, the reinforced region may have a cross-sectional dimension (e.g., width, diameter) in the range of from about 1 micrometers to about 10 cm or even 20 cm. The reinforced region may have a cross-sectional dimension in the range of about 10 micrometers to about 10 cm, or from about 100 micrometers to about 1 cm.

Without being bound to any particular theory, the improved mechanical properties of the reinforced region act to stabilize the myocardium and in turn reduce wall stresses. It is known that infarcted regions exhibit reduced wall thickness and a global change to a more spherical geometry correspond to increases in wall stress. These alterations increase the mechanical burden on the injured heart and initiate maladaptive biological processes that act together to produce heart failure. Since the increase in wall stress during systole or diastole may drive maladaptive, post-infarction remodeling processes, a reinforced region that is mechanically superior to injured or even native cardiac tissue normalizes myocardial stress distribution and reduces maladaptive post-infarction remodeling.

In one exemplary embodiment, injectable modified hyaluronic acid (HA) hydrogels were used to stiffen/thicken the infarct area to limit the associated BZ expansion, limit LV dilation, and improve global function in an established, clinically relevant ovine infarction model. Injectable formulations of HA hydrogels were designed that have similar degradation and gelation behavior to eliminate mass loss and tissue distribution as variables, yet have varied mechanical properties.

In one example, two methacrylated HA macromers (MeHA) with varying amounts of methacrylate substitution were synthesized. Methacrylated hyaluronic acid (MeHA) was synthesized as previously described (Burdick et al., *Biomacromolecules* 6(1):386-91 (2005)). Briefly, sodium hyaluronate (Lifecore, 74 kDa) was dissolved at 1 wt % in deionized water and reacted with methacrylic anhydride (Sigma) at pH 8.0 on ice for 24 hours, with varied amounts of methacrylic anhydride to influence the final macromer methacrylation. The macromer was purified via dialysis (MW 6-8 kDa cutoff) against deionized water for 72 hours and lyophilized. $^1$H NMR (Bruker) was used to determine the % methacrylation.

Figure 6:
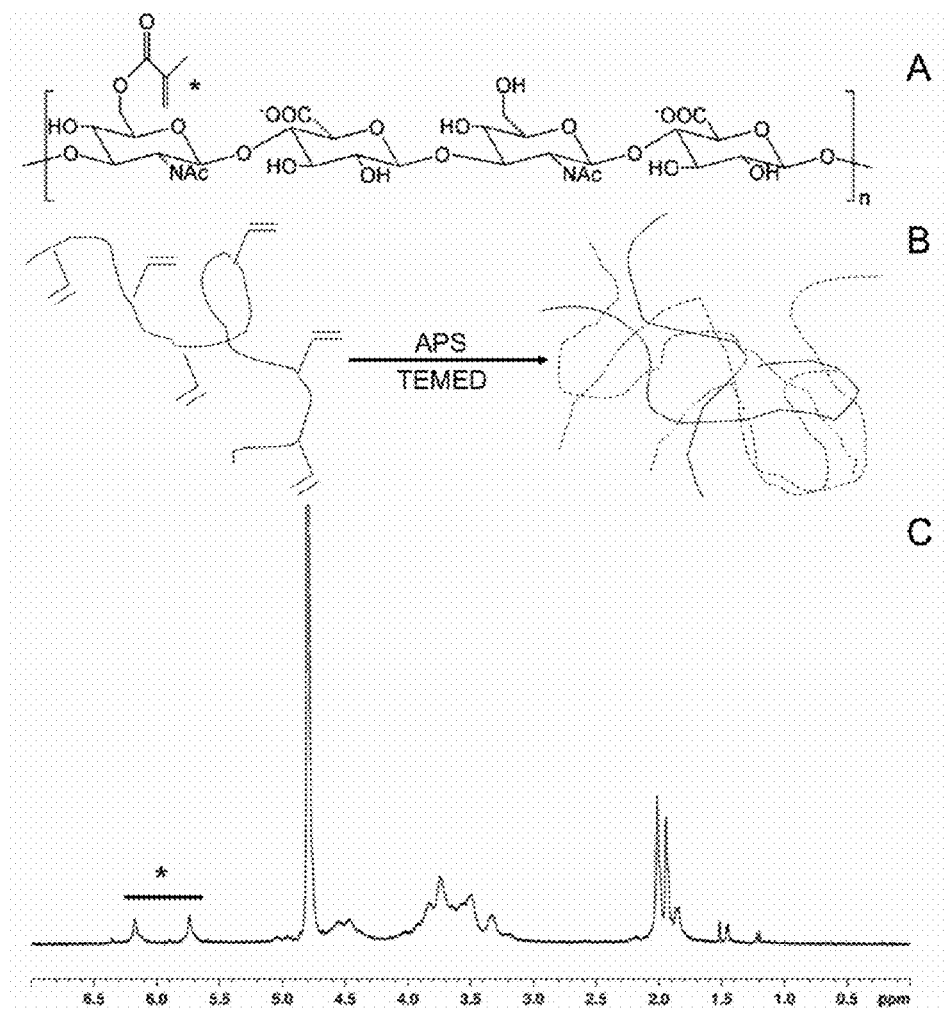
FIGS. 6A-6C concern characteristics of Methacrylated hyaluronic acid (MeHA), including chemical structure (FIG. 6A), schematic of hydrogel formation (FIG. 6B), and representative $^1$H NMR spectra of MeHA (FIG. 6C). * denotes the methacrylate group.
Figure 7:
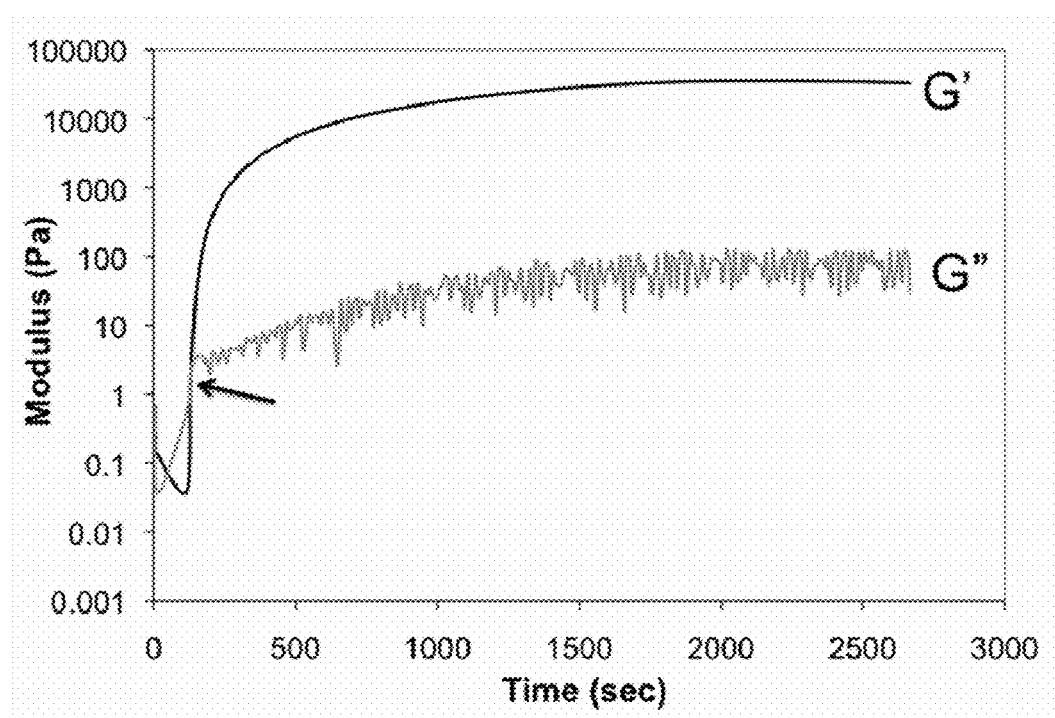
FIG. 7 illustrates a representative MeHA High (5.0 mM APS/5.0 mM TEMED) time sweep depicting gelation onset, as indicated by the arrow.

The extent of modification in these illustrative materials was found to be ~30% (referred to herein as "MeHA Low") or ~60% (referred to herein as "MeHA High") by $^1$H NMR. Exemplary hydrogels were prepared from the macromers (maintained at 4 wt %) upon combination with the bi-component redox initiation system of APS and TEMED (illustrated by FIG. 6; also illustrating the $^1$H NMR spectra of MeHA, where the * denotes the methacrylate group). Rheometry was used to monitor the storage (G') and loss modulus (G") of hydrogels formed from the different macromer and initiator combinations. FIG. 7 illustrates one representative MeHA High (5.0 mM APS/5.0 mM TEMED) time sweep depicting gelation onset, as indicated by the arrow.

A difference between G' (defined as the fourth consecutive point with <1% change) of the two hydrogels formed with identical initiator concentrations, as well as a significant difference between hydrogels formed from the same macromer but different initiator concentrations, were observed, as shown in FIG. 1A. The time for gelation onset (i.e., G'>G") decreased as the initiator concentration increased and ranged from ~2.5 to 4.5 minutes (FIG. 1B). Gelation time was not dependent on the MeHA formulation (i.e., MeHA High versus MeHA Low). FIG. 1 also illustrates the intergration of the gel (labeled by G) into cardiac tissue (labeled by E); as shown, the gel integrates well into the tissue.

The delivery and penetration of the hydrogel (with dye for visualization) was evaluated through injection into the apical region of explanted ovine left ventricle tissue. A greater distribution of the hydrogel in the tissue was observed with a lower initiator concentration and slower gelation time when compared to hydrogels formed with a higher initiator concentration and faster gelation (FIGS. 1C and 1D). The high initiator concentration yields a more rapid increase in viscosity. The 5.0 mM APS and 5.0 mM TEMED initiator combination was selected for the exemplary studies. Gel distribution was not dependent on the MeHA formulation, while initiator concentration was constant. When the hydrogel was injected in vivo and assessed 24 hours post-MI (FIG. 1E), histological staining demonstrates a clear integration of the gel within the tissue and distribution throughout cell layers (FIG. 1E).

Figure 2:
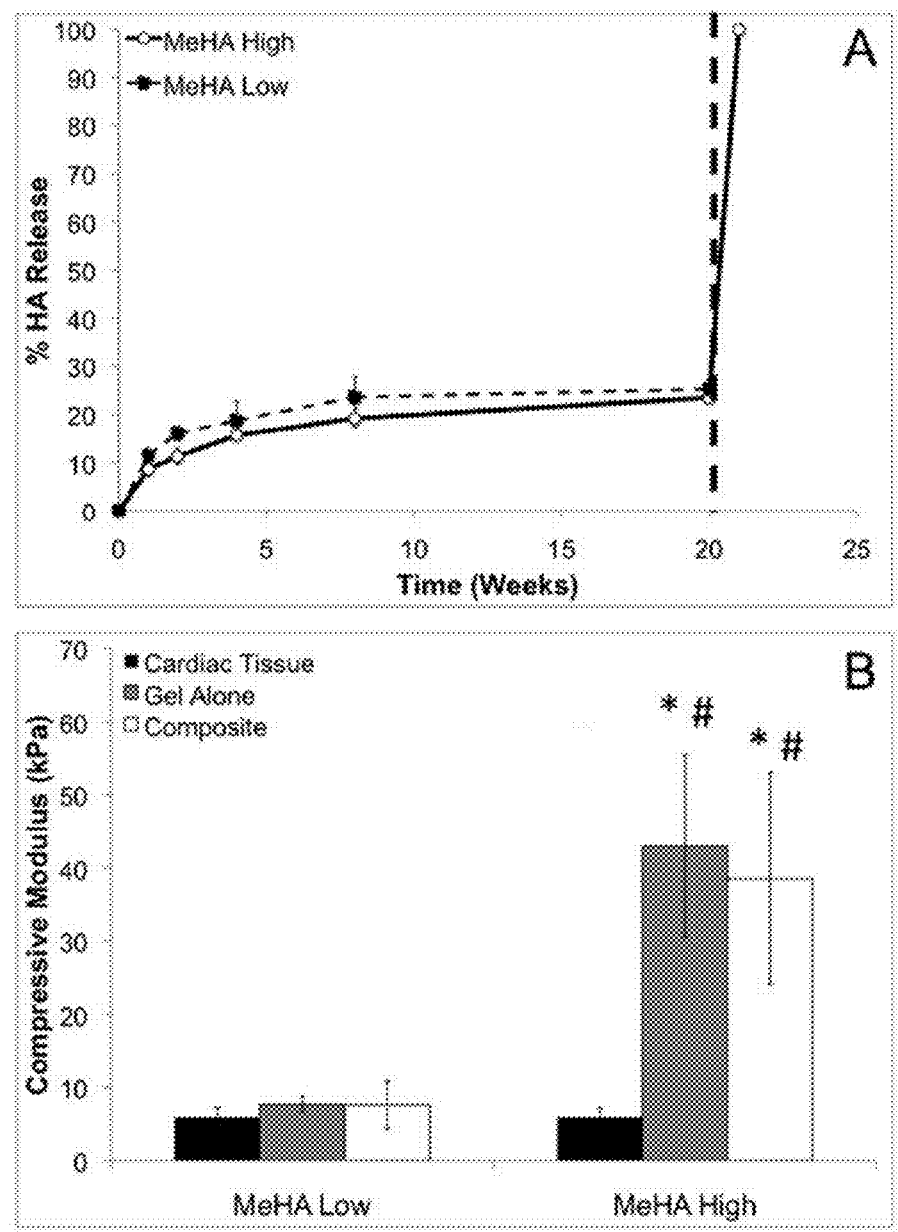
FIGS. 2A and 2B address hydrogel degradation and compressive mechanics. MeHA High (circle, solid line, n=3) and MeHA Low (square, dotted line, n=3) degradation with time. % HA release was quantified with the uronic acid (by-product of HA degradation) assay, the vertical dashed line represents the addition of 100 U/mL exogenous hyaluronidase at 20 weeks to initiate complete degradation (FIG. 2A). Cardiac tissue, MeHA hydrogel, and hydrogel/tissue composite mechanical properties. N=5 per group, data is presented as mean±standard deviation, and * denotes p<0.05 compared to cardiac tissue, # denotes p<0.05 compared to MeHA Low for the respective condition (FIG. 2B).
Figure 8:
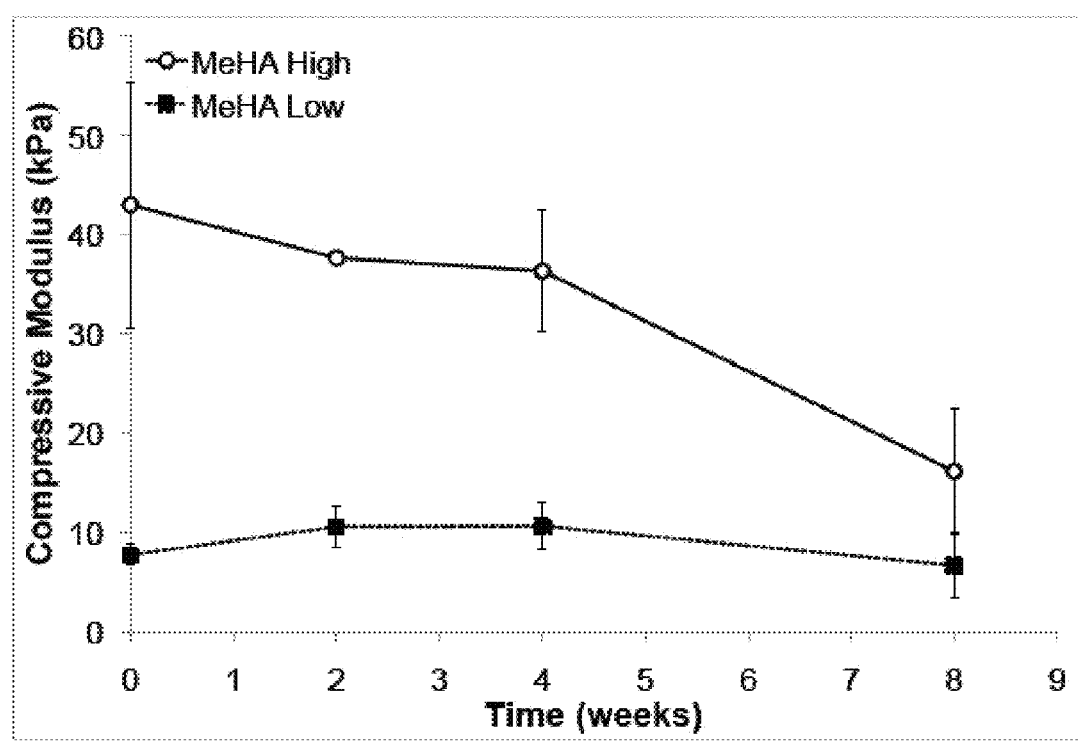
FIG. 8 illustrates the compressive modulus of MeHA High (circle, solid line) and MeHA Low (square, dashed line) with in vitro degradation over 8 weeks.

Bulk hydrogels formed from the foregoing macromer/initiator combinations lost less than 25% of their mass after 20 weeks in phosphate buffered saline at 37° C. (as measured using a uronic acid assay (Bitter et al., *Analytical Biochemistry* 1962)) and there was no statistically significant difference in the overall % HA release or profiles throughout degradation (FIG. 2A). There was a decrease in the modulus of bulk hydrogels with time, which decrease was observed with MeHA High. This is illustrated in FIG. 8, which figure illustrates the compressive modulus of MeHA High (circle, solid line) and MeHA Low (square, dashed line) with in vitro degradation over 8 weeks.

Figure 9:
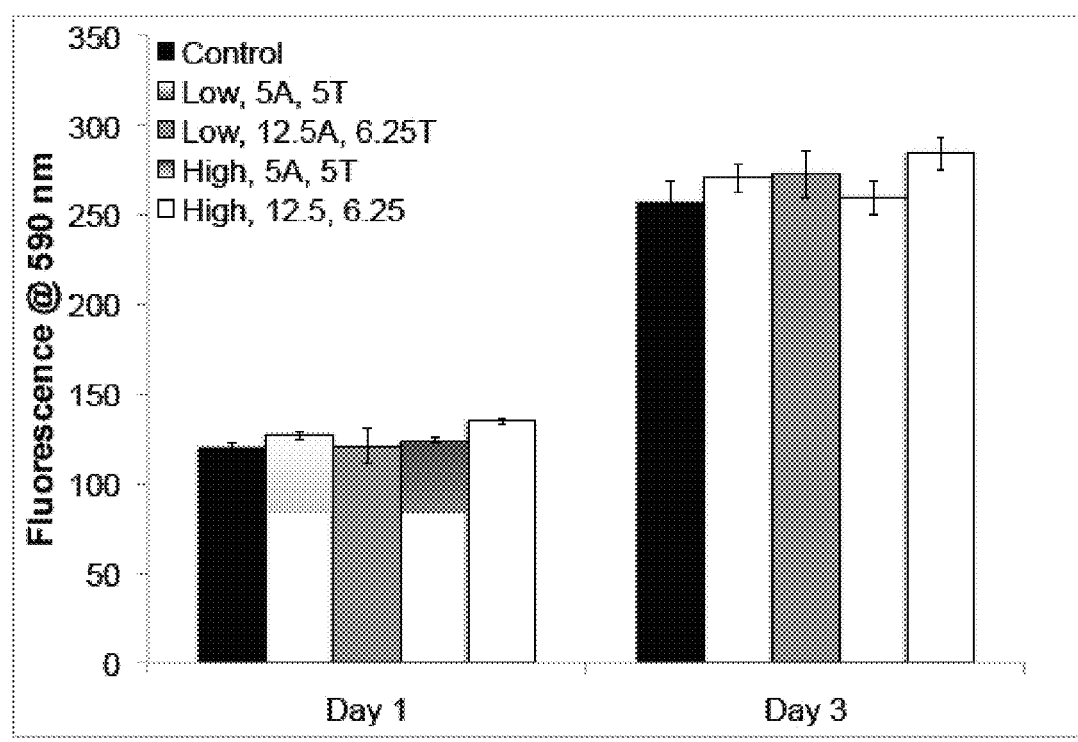
FIG. 9. In vitro cytotoxicity. Human mesenchymal stem cells were cultured in the presence of the different hydrogels in a transwell format and viability was assessed via the AlamarBlue assay. Data is plotted as mean±standard deviation. There were no statistical differences between any groups at each time-point (n=3/group/time-point).

Cytotoxicity was evaluated through exposure of seeded human mesenchymal stem cells to sterilized bulk hydrogels (formed using the same initiation conditions) in a transwell format for up to 3 days and no differences were observed with any of the gels compared to unexposed controls, as illustrated in FIG. 9 (viability was assessed via the Alamar-Blue assay). Data are plotted as mean±standard deviation. There were no statistical differences between any groups at each time-point (n=3/group/time-point).

Figure 10:
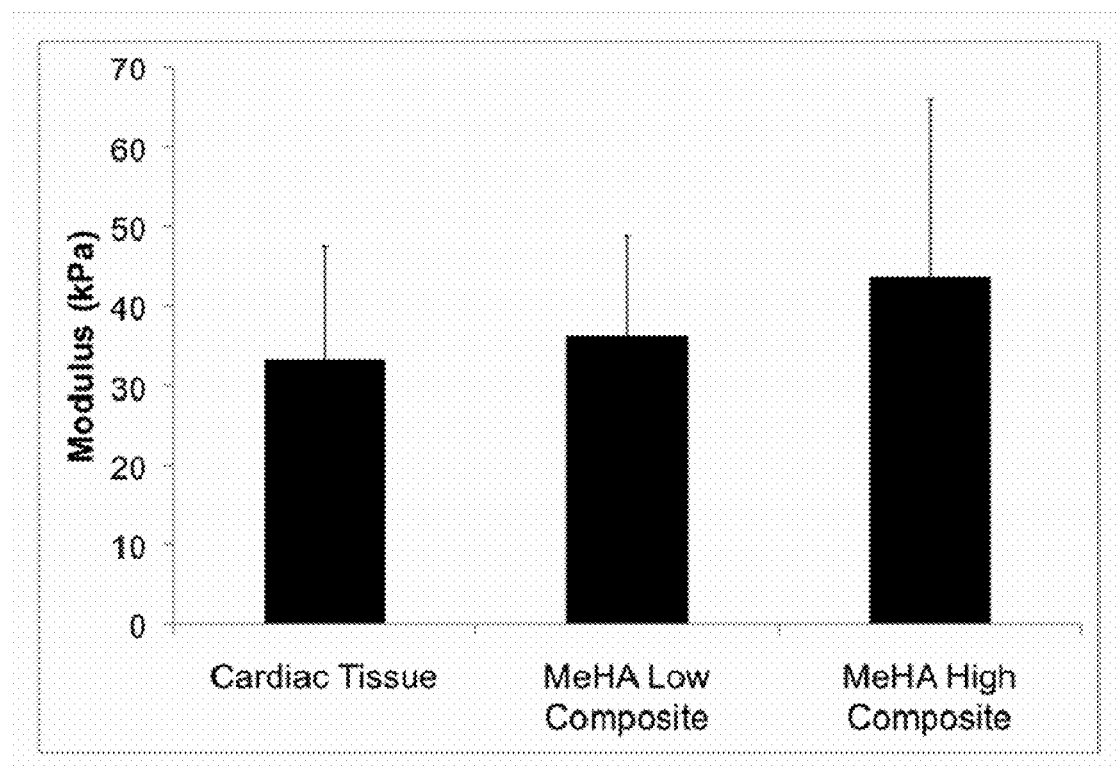
FIG. 10 shows cardiac tissue and hydrogel tissue composites moduli as determined using uniaxial tensile testing. Samples (20×5×2 mm) were prepared from the mid-wall of the left ventricle in the indicated direction followed by injection of 0.3 mL of macromer/initiator solution (if necessary). N=4-8 per group, data is presented as mean±standard deviation.

The mechanics of bulk hydrogels alone, explanted cardiac tissue alone, and hydrogel/tissue composites were also reviewed. Under compression, the modulus of untreated cardiac tissue was 5.8±1.5 kPa, whereas the bulk hydrogels had moduli of 7.7±1.0 kPa and 43.0±12.3 kPa for MeHA Low and MeHA High, respectively. The modulus of the tissue/hydrogel composites were greater than explanted cardiac tissue alone for the MeHA High group, but not for the MeHA Low group (FIG. 2B). Specifically, there was no statistical difference in the modulus between the cardiac tissue and the composite with the MeHA Low gel; however, there was a statistically significant increase in modulus with the MeHA High composite when compared to normal cardiac tissue. Similar trends were observed when the tissue/hydrogel composites underwent uniaxial tensile testing in the longitudinal direction, as in FIG. 10. That figure illustrates Cardiac tissue and hydrogel tissue composites moduli as determined using uniaxial tensile testing. Samples (20× 5×2 mm) were prepared from the mid-wall of the left ventricle in the indicated direction followed by injection of 0.3 mL of macromer/initiator solution, in some cases. N was 4-8 per group, and data are presented as mean±standard deviation.

The introduction of the reinforcement material after infarction leads to maintenance of tissue thickness as compared to unreinforced infarct samples. As described below in the examples, injection of a monomer material followed by polymerization after infarction led to tissue samples that maintained a tissue thickness that was thicker by a statistically significant margin over non-reinforced, control samples. The term "monomer" is understood to include monomers (e.g., ethylene) as well as macromers. Additionally, the introduction of a reinforcing material reduced the area of infarct relative to control, non-reinforced cardiac material.

Figure 3:
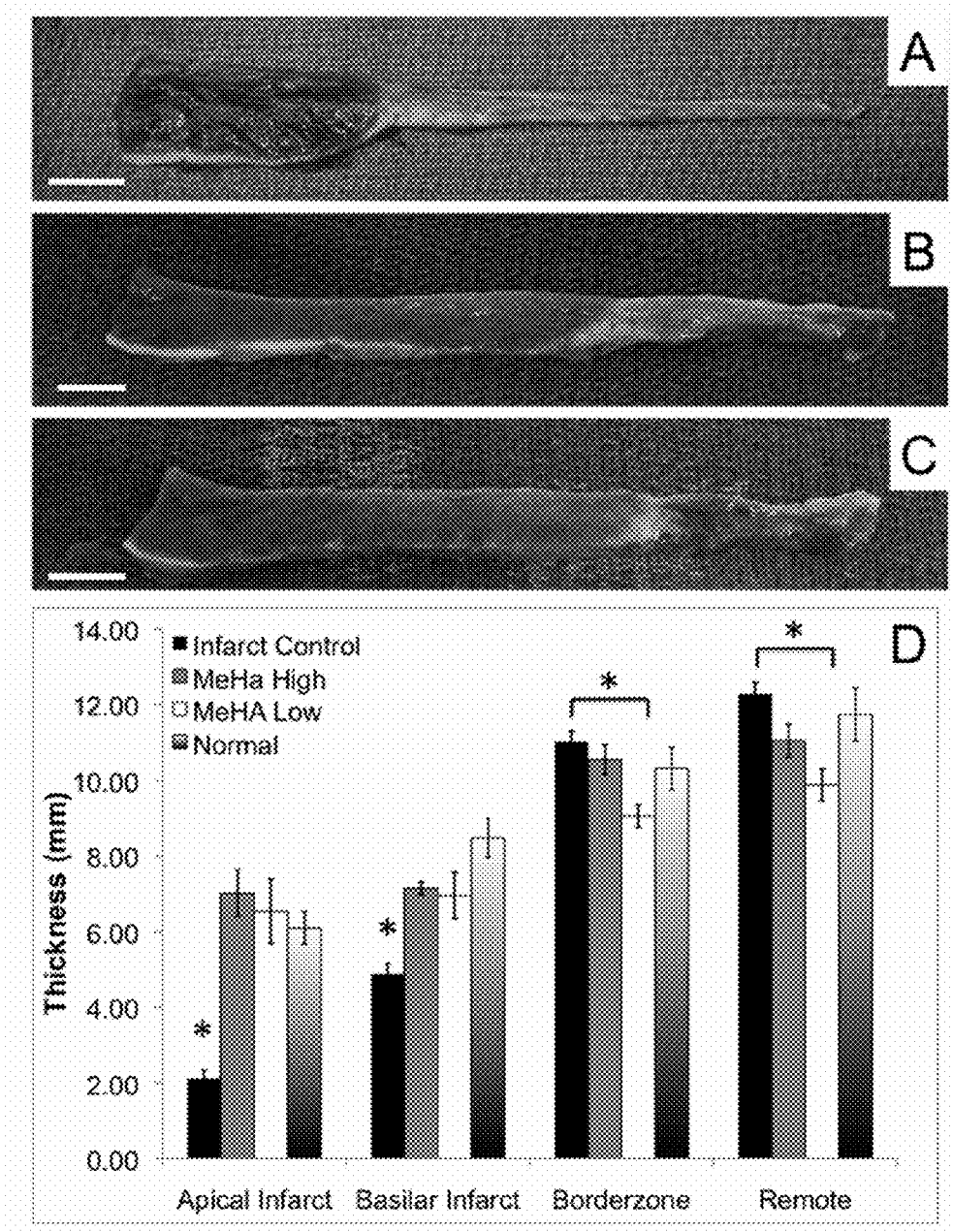
FIGS. 3A-3D illustrate how hydrogel treatment influences myocardial wall thickness. Representative samples of control infarct (FIG. 3A, n=9), MeHA High treatment (FIG. 3B, n=6), and MeHA Low treatment (FIG. 3C, n=5) 8 weeks post-MI and hydrogel injection. Quantified regional tissue thicknesses at 8 weeks (FIG. 3D, n=5 for Normal). Data is presented as mean±standard error of the mean and * denotes p<0.05 compared to all other groups in the same region. Scale bar=10 mm.
Figure 11:
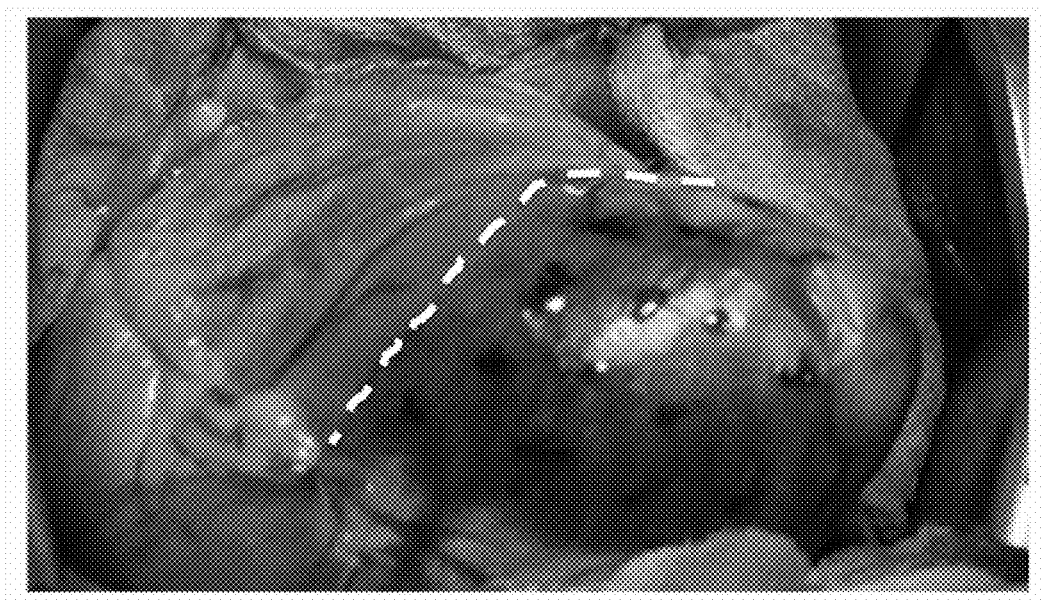
FIG. 11 shows a sheep heart (as viewed from left thorocotomy) depicting the infarct area (discolored region to the right of the dashed line) and the injection sites (dots).

Injection of the MeHA hydrogels 30 minutes after infarction led to maintenance of tissue thickness compared to control infarct samples. FIG. 11 is representative, showing a sheep heart (as viewed from left thorocotamy) depicting the infarct area (discolored region to the right of the dashed line) and the injection sites (dots). This thickness maintenance was evident upon sacrifice at 8 weeks (FIGS. 3A, 3B, and 3C). FIG. 3A is a representative samples of a control infarct sample (n=9). FIG. 3B is a representative sample of a sample with MeHA High treatment (n=6). FIG. 3C is a representative sample of MeHA Low treatment (n=5). All samples are taken from subjects 8 weeks post-MI and hydrogel injection.

FIG. 3D illustrates quantified regional tissue thicknesses at 8 weeks (n=5 for Normal). Data is presented as mean±standard error of the mean and * denotes p<0.05 compared to all other groups in the same region. Scale bar=10 mm. The regional thickness from the apex to the base was quantified and demonstrated significant differences in tissue thickness in the apex (7.02 and 6.54 mm) and basilar infarct (7.15 and 6.96 mm) regions for MeHA High and MeHA Low hydrogel injections, respectively, compared to control infarct (2.13 and 4.89 mm) apex and basilar infarct regions, respectively, as shown in FIG. 3D.

Figure 4:
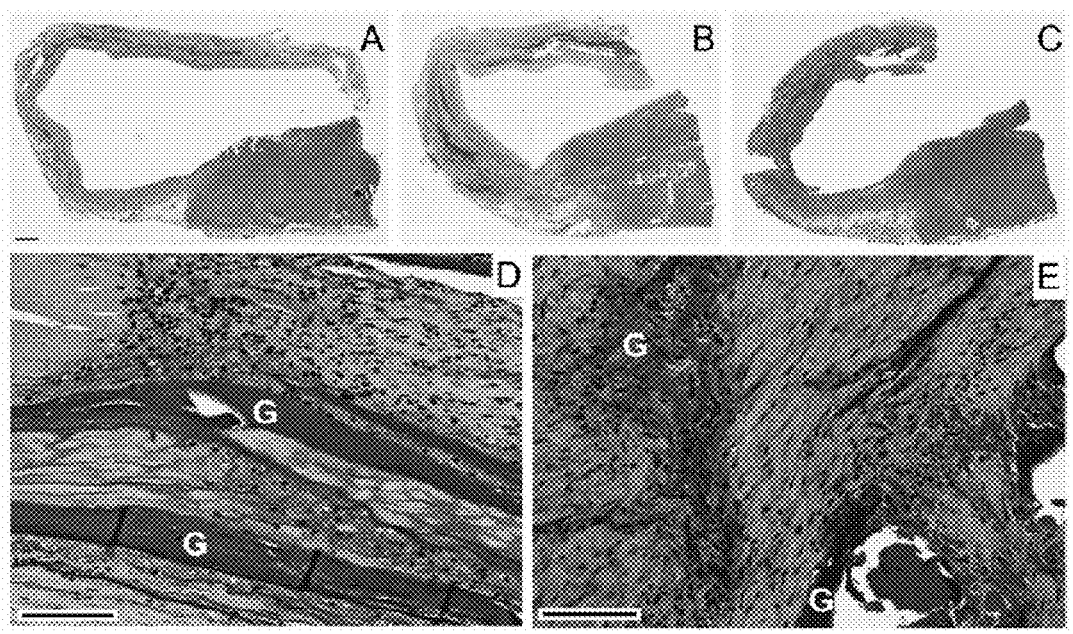
FIGS. 4A-4E provide histological images at 8 weeks post-MI and injection. Representative hematoxylin and eosin stained samples of control infarct (FIG. 3A), MeHA High (FIG. 4B, FIG. 4D) and MeHA Low (FIG. 4C, FIG. 4E) treatment where the gel (labeled with G) stains purple. Scale bar=1 mm (FIG. 4A-FIG. 4C) or 100 µm (FIG. 4D, FIG. 4E).

The prevention or reduction of tissue thinning is also evident upon examination of the representative histological images in FIG. 4. That figure illustrates representative hematoxylin and eosin stained samples of control infarct (A), MeHA High (B,D) and MeHA Low (C,E) treatment where the gel (labeled with G) was stained purple. The scale bar is 1 mm for 4A-4C, and is 100 micrometers for 4D-4E. The magnified images of samples with MeHA High (FIG. 4D and FIG. 12D) and MeHA Low (FIG. 4E and FIG. 12E) treatment depict that the gels are present and maintain their integration with the tissue at 8 weeks.

Figure 12:
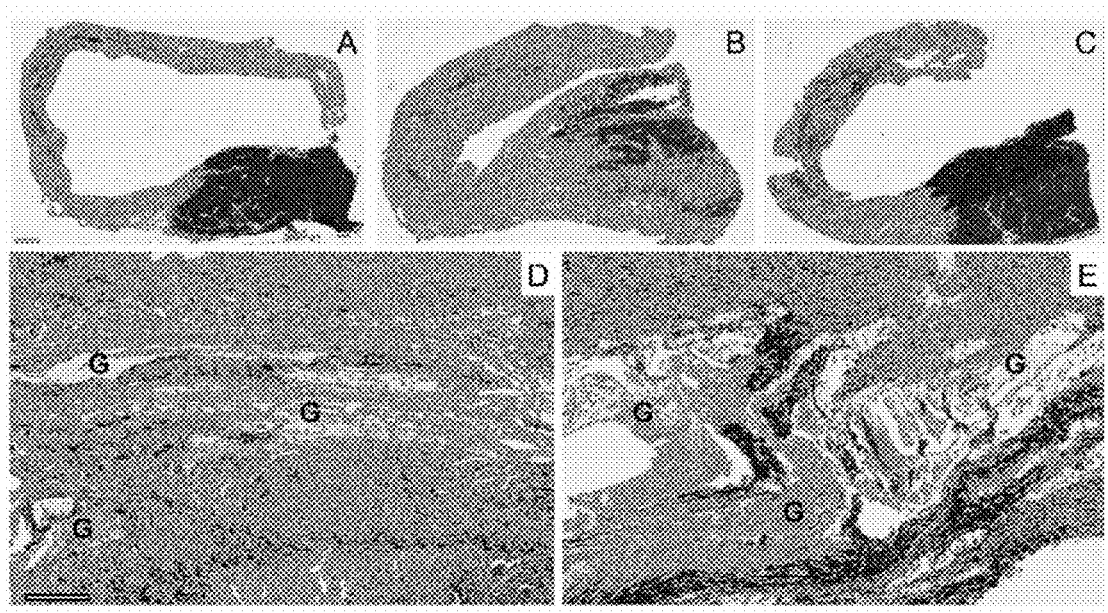
FIGS. 12A-12E provide histological images at 8 weeks post-MI and injection. Representative trichrome stained samples of control infarct (FIG. 12A), MeHA High (FIG. 12B, FIG. 12D) and MeHA Low (FIG. 12C, FIG. 12E) treatment where the gel (labeled with G) stains light blue. Scale bar=1 mm (FIGS. 12A-C) or 200 μm (FIG. 12D, FIG. 12E).

FIG. 12 illustrates histological images at 8 weeks post-MI and injection. Representative trichrome stained samples of control infarct (A), MeHA High (B,D) and MeHA Low (C,E) treatment where the gel (labeled with G) was stained light blue. Scale bar=1 mm (A-C) or 200 μm (D,E).

The length of the anteroapical wall motion abnormality immediately after coronary occlusion and before injection was similar in all groups, indicating that the stimulus for remodeling (i.e., initial infarct size) was comparable between the three groups (FIG. 5A). However, the infarct area at the time of sacrifice was reduced with MeHA treatment (23.9% MeHA High, p<0.05 and 26.4% MeHA Low) compared to the control infarct (28.6%) indicating that the treatment groups experienced less infarct expansion during the 8 week follow-up period (FIG. 5A). The non-statistically significant trend toward smaller lengths of the anteroapical wall motion abnormality in the MeHA High group lend support to this conclusion (FIG. 13).

Figure 5:
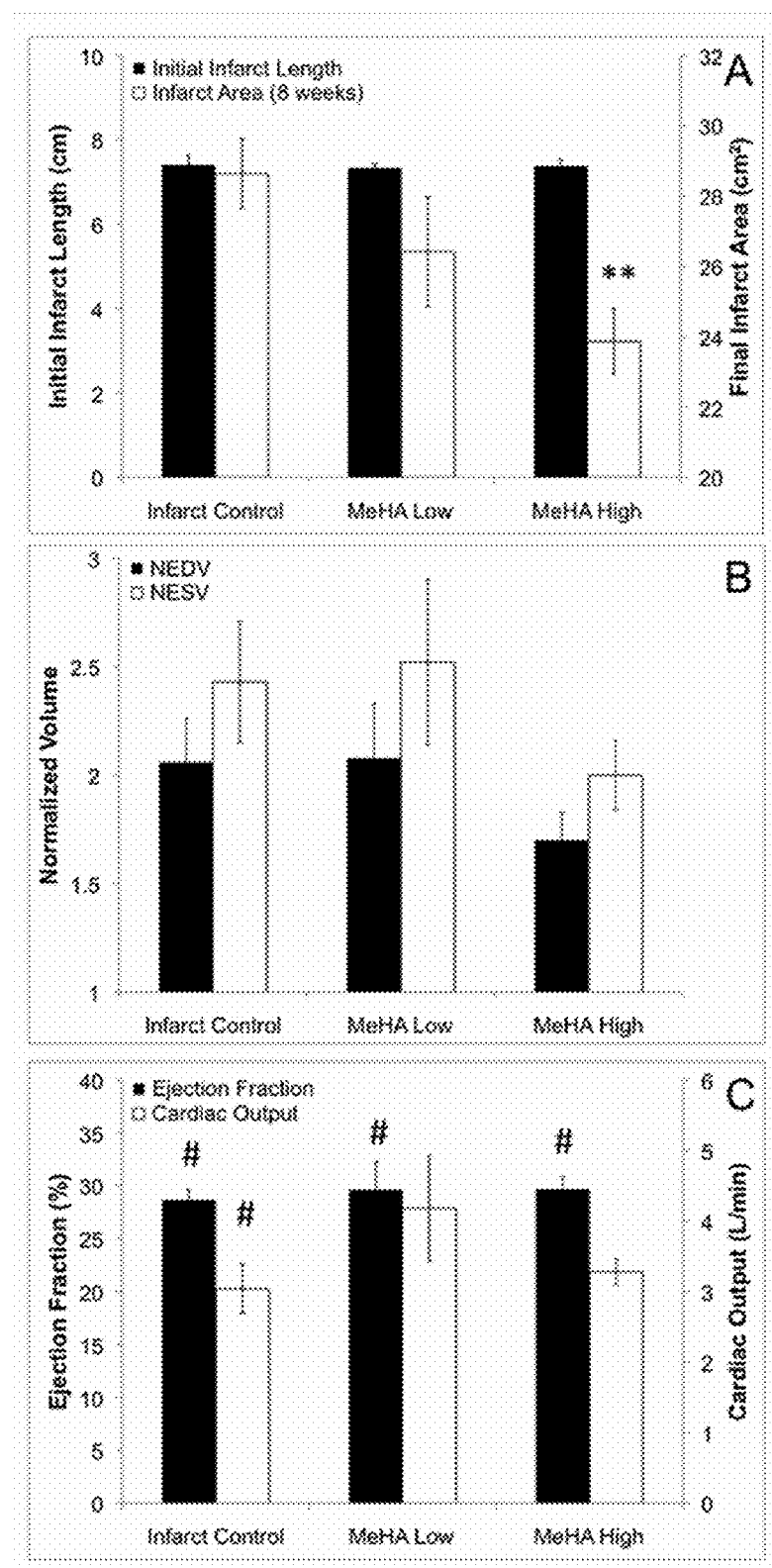
FIGS. 5A-5C show quantified infarct dimensions, in vivo volume, and functional metrics for control infarct (n=9), MeHA High treatment (n=6), and MeHA Low treatment (n=5) for initial infarct length and infarct area at 8 weeks (FIG. 5A), for normalized end diastolic volume normalized end systolic volume (FIG. 5B), and cardiac output and ejection fraction (FIG. 5C). Data is presented as mean±standard error of the mean and * denotes p<0.05 versus control infarct and # denotes p<0.05 versus respective baseline value.

FIG. 5 also illustrates in vivo volume and functional metrics for control infarct (n=9), MeHA High treatment (n=6), and MeHA Low treatment (n=5) for normalized end diastolic volume normalized end systolic volume (B), and cardiac output and ejection fraction (C). The data are presented as mean±standard error of the mean and * denotes p<0.05 versus control infarct and # denotes p<0.05 versus respective baseline value.

The reinforced region thus attenuates adverse heart remodeling and improves cardiac function relative to unreinforced cardiac tissue that has suffered an infarct event. This reduced remodeling and improved cardiac function may be assessed by normalized end diastolic volume, normalized end systolic volume, ejection fraction, and other cardiac function parameters; the measurements investigated in FIG. 5 should not be construed as limited the scope of the present disclosure.

Real-time 3D echocardiography may be used to assess the LV dimensions and cardiac function for each animal prior to and immediately after (i.e., baseline) infarction. The normalized end diastolic volume (NEDV) and normalized end systolic volume (NESV) increased for all groups after 2 weeks, with the MeHA High treatment group tending to have the smallest changes in volume (FIG. 13). As shown in FIG. 5B, a similar trend was observed after 8 weeks, with the MeHA High treatment group again demonstrating an improvement in NEDV (1.7, FIG. 5B) and NESV (1.9, FIG. 5B) compared to the infarct control (2.1 and 2.4, respectively) and the MeHA Low treatment group (2.1 and 2.5, respectively). This improvement was even more dramatic upon stress testing with Dobutamine (2.5 and 5.0 mg/kg/min), which was conducted prior to sacrifice (FIG. 13).

The cardiac output (CO) was reduced for all groups at 2 and 8 weeks following MI, although this difference was only statistically different from the baseline for the control infarct group (FIG. 5C and FIG. 13). A reduction in the ejection fraction (EF) at 2 and 8 weeks was also observed for all groups relative to their respective baseline values (FIG. 5C and Table 1). Stress testing prior to sacrifice demonstrated a greater improvement in EF of the MeHA High treatment group (FIG. 13).

The present disclosure also provides kits. The kits suitably include an injector adapted to deliver fluid to cardiac tissue and a quantity of polymerizable material, the polymerizable material being selected for delivery to cardiac tissue.

Injectors may be catheters, syringes, pumps, and the like. The polymerizable material may be pre-loaded into the injector. Alternatively, the polymerizable material may be separately packaged and then loaded into the injector. The injector may include one, two, or more chambers for containing and delivering material to a subject. For example, an injector may include a chamber for containing monomer and also a chamber or chambers for containing initiator and crosslinker.

Suitable polymerizable materials (monomers) are described elsewhere herein, and include methacrylated hyaluronic acid, methacrylated/acrylated poly(ethylene glycol), acrylated poly(ethylene glycol), methacrylated/acrylated poly(vinyl alcohol), methacrylated/acrylated chitosan, metahcrylated/acrylated cellulose, poly(n-isopropryl acrylamide), methacrylated/acrylated alginate, methacylated/acrylated heparin, or any combination thereof.

Kits suitably include a quantity of crosslinker, a quantity of initiator, or both. The initiator or cross-linker may be present in a multi-barrel injector with the monomer such that the materials are delivered to the subject at essentially the same time. The initiator or crosslinker may also be delivered to the subject via an injector different from the injector used to deliver the monomer. Kits may include one, two, or more portions of polymerizable material. The portions may differ from one another in terms of monomer concentration, monomer composition or both.

The kits may also include additional therapeutic agents, such as growth factors, protease inhibitors, and the like. Such therapeutic agents include stems cells (e.g., mesenchymal, embryonic, fetal, adult, amniotic, induced pluripotent), platelets, plasma components (including concentrated plasma components), and the like.

Exemplary Results

The following data are from one illustrative embodiment of the present invention. These data and results are illustrative only and should not be understood to limit the scope of the present disclosure.

The LV remodeling that occurs post-MI is a complex process and increased understanding of this process, as well as the impact of various treatment paradigms is needed to develop valuable therapies to impact patient outcomes and welfare. LV remodeling evolves with time post-MI to involve myocardium more remote from the infarct in a process known as borderzone expansion. The reduced wall thickness in the infarct region and a global change to a more spherical geometry correspond to increases in wall stress. These alterations increase the mechanical burden on the injured heart and initiate maladaptive biological processes that act together to produce heart failure. Furthermore, the influence of specific material properties on LV remodeling response has not been explored experimentally and is not well understood. This is partially due to the difficulty in developing materials that can systematically investigate the influence of one property (e.g., mechanics) without altering other potentially confounding parameters (e.g., mass loss).

One exemplary (i.e., non-limiting) system studied was HA hydrogels. In this system, the mechanical properties were modified through alteration in the number of reactive methacrylate groups (i.e., MeHA Low versus MeHA High) on the MeHA macromer. After crosslinking with a APS/TEMED redox initiation system, the extent of modification leads to variations in the crosslinking density of the hydrogels, which correlates to changes in bulk mechanical properties, while maintaining the same concentration of the material. Changes in the initiator concentration (i.e., onset of gelation) led to variations in the distribution of the hydrogel within the myocardial tissue, another parameter that may be important in therapy development, as well as the mechanics of a specific MeHA formulation. However, the time for gelation was not dependent on the extent of methacrylation. Mass loss also did not change between the two MeHA formulations. While the hydrogels undergo some bulk hydrolytic degradation (due to ester bonds in the methacrylate group) and the compressive moduli of the hydrogels change moderately with time, they remain greater than (MeHA High) or similar to (MeHA Low) cardiac tissue even after 8 weeks of in vitro degradation. Thus, this illustrative system allows for investigation of the influence of hydrogel mechanics on the resulting therapeutic outcomes for treating MI, without variations in material amount, degradation, or tissue distribution to confound the findings.

The user may perform two or even more "rounds" of reinforcing cardiac tissue. For example, the user may introduce a first quantity or quantities of reinforcing material to the heart. After a few days, weeks, or even months, the user may introduce additional reinforcing material to offset any degradation that the first quantity of reinforcing material may have experienced. The additional material may be the same as the first material (i.e., same combination of monomer and initiator), or may be a different monomer system. In this way, the user may maintain cardiac reinforcement for the subject and can tailor cardiac reinforcement, depending on the subject's condition over time.

Investigation of the mechanics of cardiac tissue prior to and after injection of the hydrogels revealed an increased modulus with hydrogel injection, dependent on the MeHA modification. A constant initiator system of 5.0 mM APS/5.0 mM TEMED initiator combination was selected. Thus, compression was used to minimize non-uniformity of the samples and it was possible to core the samples that appeared uniform. Similar trends were observed upon uniaxial tensile testing of tissue/hydrogel composites in the longitudinal direction.

Samples were isolated from the mid-wall. Histological evaluation of a hydrogel/tissue composite at 24 hours post-injection in vivo demonstrated stable gel formation and integration of the gel within the tissue, which was observed even at 8 weeks post-injection. Thus, the stability of the materials indicates that one difference between the two groups was the mechanical properties of the hydrogel. Cellular response to MeHA was limited, with no evidence of increased macrophage or myofibroblast infiltration. Without being bound to any single theory, the change in infarct expansion and functional properties appear to relate to the properties of the injectate rather than a biologic response to the material. A finite element study simulation of the theoretical impact of injection of material into the myocardium after MI illustrates the suspected stress reduction potential of intramyocardial stiffening.

Stiffer materials may bear more of the load in the remote and borderzone regions, resulting in a decrease in stresses within these regions. Accordingly, comparatively stiff materials are considered especially suitable for the disclosed methods. Using a closed-loop lumped-parameter model of the ovine cardiovascular system, a reduction in compliance in the infarct area (i.e., infarct stiffening) reduces dilation of the LV and improve EF. For this reason, specific formulations were investigated to form hydrogel/tissue composites that have similar (MeHA Low) and greater (MeHA High) moduli than native cardiac tissue. Hydrogels were injected 30 minutes post-infarct into 20 injection sites in the apex and borderzone region and outcomes were assessed after 2 and 8-weeks, as well as with Dobutamine stress evaluation immediately prior to sacrifice. To limit animal mortality, it was decided to intervene at 30 minutes post-infarction.

The exemplary MeHA system was used to isolate and explore one variable (e.g., injected hydrogel mechanics) in order to systematically evaluate the resulting impact on infarct expansion and remodeling.

A statistical difference in wall thickness in the apex and basilar infarct regions was evident for both MeHA treatment groups relative to infarct control. These groups had wall thicknesses similar to non-infarct controls. This drastic difference in tissue thickness is further evident upon examination of the histological images. Although infarct thicknesses increased in both treatment groups relative to control, there was less infarct expansion and reduced LV remodeling with the MeHA High formulation. Without being bound to any single theory, the properties of the injected material (i.e., increased stiffness) may contribute to stress reduction and not to infarct stiffening alone.

Global LV geometry was evaluated using real-time 3D echocardiography. At the 2-week and 8-week time points, an increase in NEDV and NESV for all groups was observed. The MeHA High treatment group had the smallest changes in volume compared to the control infarct and MeHA Low treatment groups. Furthermore, the difference in the volume change from the 2-week to the 8-week time point was lowest for the MeHA High treatment group for both NEDV and NESV. The improvement in LV volume in the MeHA High treatment group is seen clearly upon the stress testing completed prior to sacrifice at 8 weeks. These observations are of interest since ESV (end systolic volume) is indicative of adverse effects post-MI. LV function was assessed through monitoring CO and EF throughout the study. The control infarct group had statistically different values at the 2-week and 8-week follow-ups, whereas both of the MeHA treatment groups did not. A decrease in EF was observed for all treatment groups at the 2-week and 8-week follow-ups. The MeHA High treatment group tended to have improved EF, shown clearly upon stress testing.

In sum, there were salutary effects associated with differences in the mechanics of the injectable hydrogels developed to limit infarct expansion and suppress the LV remodeling response that occurs post-MI. The higher modulus hydrogel treatment group demonstrated less infarct expansion and reduced LV dilation, as well as improved function compared to lower modulus hydrogel and infarct control groups. Higher modulus MeHA High hydrogel effectively stabilized the myocardium and reduce wall stresses compared to the lower MeHA Low treatment group. The MeHA Low group experienced benefits as well, and the present disclosure should not be understood as limiting the provided methods, kits, and materials to the MeHA High group or to materials having properties similar to MeHA High. The modulus of the tissue/MeHA Low composite group is similar to that of the excised cardiac tissue, it is likely that these values are closer to the passive material properties of the myocardium during diastole, whereas the modulus of tissue/MeHA High composite is closer to passive myocardial material properties at end systole. Since the increase in wall stress during systole is likely driving the maladaptive remodeling process, the tissue treated with MeHA High is capable of normalizing myocardial stress distribution.

This disclosure also evaluates the impact in vivo of the effect of injectable material properties on the post-MI LV remodeling response. This provides information towards the development of hydrogels for treatment of LV remodeling.

Supporting Information—Techniques and Protocols

The animals used in this work received care in compliance with the protocols approved by the Institutional Animal Care and Use Committee at the University of Pennsylvania in accordance with the guidelines for humane care (National Institutes of Health Publication No. 85-23, revised 1996).

In general, MeHA (4 wt %) was dissolved in phosphate buffered saline (PBS) with various concentrations of ammonium persulfate (APS, 5.0 or 12.5 mM, Sigma) and N,N,N',N'-tetramethylethylenediamine (TEMED, 5.0 or 6.25 mM, Sigma). Gelation onset (n=3) was quantified by monitoring the storage (G') and loss (G") moduli with time using an AR2000ex Rheometer (TA Instruments) at 37° C. under 1% strain and 1 Hz in a cone and plate geometry (1°, 20 mm diameter). MeHA/APS and MeHA/TEMED solutions were loaded into different barrels of a dual barrel syringe and crosslinked by expulsion and mixing from the syringe. Compression testing was completed on hydrated samples (5 mm diameter, n=3) using a Dynamic Mechanical Analyzer (Q800 TA Instruments) at a strain rate of 10% $min^{-1}$ Degradation (n=3 per time point) in PBS at 37° C. was monitored using an uronic acid assay (27) and 100 units of exogenous hyaluronidase per mL PBS was added at 20 weeks for complete degradation of the hydrogels. Cytotoxicity was evaluated as described elsewhere herein. For in vivo assessment, the lyophilized form of MeHA was sterilized upon exposure to germicidal ultraviolet light for 1 hour and subsequently dissolved in sterile PBS. APS and TEMED solutions were sterile filtered prior to use in vivo.

The delivery and penetration of the injected hydrogel into normal (not infarcted) myocardial tissue was investigated using explanted ovine myocardial tissue from the LV apex (i.e., the intended infarct region). 125 µM methacryloxethyl thiocarbamoyl rhodamine B was added for visualization purposes. This dye is both macroscopically visible and crosslinks into the hydrogel. To confirm gelation within the tissue, 0.3 mL of the macromer/initiator solution with dye was injected into the LV apex. After 30 minutes post-injection, biopsy punches were used to remove 5 mm diameter disks of tissue or tissue containing hydrogel composite for compression testing (n=5 per group from multiple samples from two hearts), as above. Please refer to the Supplemental Material for detailed methods regarding uniaxial tensile testing.

Infarction Model and In Vivo Assessment.

A clinically relevant ovine model of infarction and LV remodeling was used to assess the impact of the injected hydrogels. Twenty-one adult male Dorset sheep (35-40 kg) were anesthetized. The arterial, ventricular, and pulmonary artery pressures and electrocardiogram were monitored continuously throughout the procedure. A left thorocotamy was performed to expose the heart. Baseline echocardiographic and hemodynamic data were obtained. Infarction was induced via ligation of the left anterior descending and the second diagonal coronary artery in such a manner as to create an infarct the basal extent of which was 40% of the distance from the apex to the base of the heart. This procedure previously demonstrated the creation of a reproducible, moderately sized infarct involving ~20% of the LV mass at the anteroapex.

Animals were split into the following three cohorts: Infarct Control (n=9), MeHA High (n=7), and MeHA Low (n=5). Historical data of Normal (non-infarct) tissue thickness was used for comparisons. Cohorts receiving MeHA treatment received 20 injections of 0.3 mL macromer/initiator solution at 3 minutes post-mixing immediately following the echocardiograph at 30 minutes following infarction.

It should be noted that the number of injections and the volume of each injection are illustrative only and are not limiting on the present disclosure. Depending on the cardiac tissue being treated (i.e., size of heart, size of infarction, and the like), the user may employ more or less than 20 injections. The volume of material per injection may also be varied, depending on the tissue being treated. The volume of material introduced may be from 0.01 mL per injection to about 15 mL per injection, or from 0.1 mL per injection to about 5 mL per injection, or from 0.5 mL to about 2 mL per injection. The user of ordinary skill in the art will encounter little difficulty in determining the suitable number of injections and volume of material introduced with each injection.

The injection sites were uniformly distributed within the ischemic territory and located at a depth of approximately 2 mm into the mid-wall of the myocardium. Echocardiographic data were collected and analyzed as previously described.

Echocardiographic and hemodynamic data were collected again at two weeks post-infarct, as well as at 8 weeks. Animals also underwent dobutamine (2.5 and 5.0 mg kg$^{-1}$ min$^{-1}$) stress echocardiographic testing at 8 weeks. Following these evaluations, animals were sacrificed, the hearts were harvested, and the infarct thickness was measured with a digital micrometer. Samples were also collected and fixed for histological analysis using hematoxylin and eosin staining, as well as Mason's trichrome staining One MeHA High treatment subject was sacrificed at 24 hours post-injection and processed for histology in order to evaluate gel distribution in vivo.

Statistical Analysis

Data are presented as mean±standard deviation or mean±S.E.M. as indicated in the respective figure caption. For hydrogel characterization experiments, differences between groups were assessed using the Student's t-test. Changes in tissue dimensions as well as echocardiograph and LV function readings, were assessed using a one-way ANOVA with Tukey's post-hoc evaluation. Echocardiographic and LV function readings were compared using a paired t-test for comparisons to baseline values for a respective group. For all comparisons, p<0.05 was considered to be statistically significant.

Cytotoxicity Evaluation

Cytotoxicity of the formed gels was evaluated by exposure to human mesenchymal stem cells (Lonza, 6,000 cells cm$^{-2}$) in a transwell format (n=3 per group). Hydrogel disks were sterilized upon exposure to germicidal ultraviolet light for 1 hour and placed into a transwell insert into a well 24 hours after seeding. The AlamarBlue fluorescence assay (10% in media) was used to quantify viability at days 1 and 3 post-exposure to the hydrogels.

Uniaxial Tensile Testing

Samples (20×5×2 mm, n=4-8 per group from 4 different hearts) were removed from the mid-wall of the left ventricle of explanted (not infarcted) tissue in the longitudinal directions. Uniaxial testing was completed using an Instron 5848 Microtester with a 50 N load cell and equipped with custom grips and a phosphate buffered saline reservoir. A 0.05 N preload was applied for 60 seconds. Samples were preconditioned with 15 cycles of 0.005% of gauge length at 0.1% sec$^{-1}$ followed by a ramp to failure at 0.1% strain sec$^{-1}$. The modulus was determined as the slope between 10-15% strain (the linear region) of the resulting stress versus strain curve using a custom Matlab program.

Echocardiographic Analysis

Briefly, transapical epicardial real-time three-dimensional echocardiography was performed through the left thorocotamy using a Philips IE 33 platform with a 7 MHz ultrasound probe (Philips Medical Systems, Bothell, Wash.). Full volume 3D datasets were acquired. These were exported to a dedicated workstation for image manipulation and analysis using QLAB 3D Advanced Quantification software (Philips Medical Systems, Bothell, Wash.). The three dimensional image acquired was manipulated to display two orthogonally related long axis views, bisecting each other on the central long axis of the left ventricle. Ventricular volumes were obtained according to the software manufacturer's recommended method: in both end diastole (defined as the frame prior to closure of the mitral valve) and in end systole (defined as the frame prior to closure of the aortic valve), the basal and apical limits of the left ventricle are defined by manually placing reference points on the image in the two orthogonally related long axis views. The software then defines the interface between the endocardium and left ventricular cavity and thus the left ventricular envelope by inserting splines to connect the manually inserted reference points for each of these frames.

The 3D image for each of these two time points may then be rotated about its long axis and thus the line defining the endocardial envelope of the left ventricle may be manually fine tuned to correct for interpolation error. Once these two frames are traced in this manner the remaining frames are traced in sequence by means of automated contour detection. The resulting 4-dimensional LV model is then automatically divided into the 17-segment model of the American Society of Echocardiography with the global and segmental volume-time curves being exported to Microsoft Excel. At each time point, global end-diastolic and end-systolic volumes were defined as the maximum and minimum LV cavity volumes, respectively. Global ejection fraction was defined as [(EDV−ESV)/EDV]. The length of the anterior apical wall motion abnormality (i.e. infarct length) was measured in the 2 dimensional (2D) apical 2 chamber view. A pulmonary artery catheter was used to measure cardiac output via the thermodilution method.

Monomer material may be injected epicardially or endocardially, depending on the user's needs. Epicardial injection may be effected tranvenously or transarterially. Initiator concentration may be tailored depending on the delivery route. For example, a comparatively long catheter used for endocardial delivery may effect a delayed gelation time. Alternatively, a short needle for epicardial injection may be used with a material having a comparatively faster gelation time.

What is claimed:

1. A method of treating a subject, comprising:
   delivering a monomer into myocardial cardiac tissue comprising an infarction or other myocardial injury; and
   polymerizing at least a portion of the monomer to form a reinforced region of the cardiac tissue, the reinforced region comprises a compressive modulus, an elastic modulus, or both, that is between 1.1 and 10 times that property of the untreated region.

2. The method of claim 1, wherein the cardiac tissue comprises the myocardial wall.

3. The method of claim 2, wherein the monomer is delivered to the interior of the myocardial wall.

4. The method of claim 1, further comprising locating the infarction within the cardiac tissue.

5. The method of claim 4, further comprising locating the infarction within any of the left ventricle, the right ventricle, the left atrium, the right atrium, the aorta, or any combination thereof.

6. The method of claim 1, further comprising locating an infarcted area of the heart or weakened area of the heart that causes a heart valve to leak.

7. The method of claim 6, wherein the heart valve comprises the mitral valve, the tricuspid valve, or both.

8. The method of claim 4, further comprising delivering the monomer to the infarction.

9. The method of claim 1, wherein the monomer comprises methacrylated hyaluronic acid, methacrylated/acrylated poly(ethylene glycol), acrylated poly(ethylene glycol), methacrylated/acrylated poly(vinyl alcohol), methacrylated/acrylated chitosan, methacrylated/acrylated cellulose, poly(n-isopropryl acrylamide), methacrylated/acrylated alginate, methacylated/acrylated heparin, or any combination thereof.

10. The method of claim 1, wherein the reinforced region comprises a hydrogel.

11. The method of claim 9, wherein the monomer comprises methacrylated hyaluronic acid.

12. The method of claim 9, wherein the reinforced region comprises a compressive modulus, an elastic modulus, or both, that is between about 2 and about 10 times that property of native cardiac tissue.

13. The method of claim 1, wherein the reinforced region improves cardiac function relative to unreinforced cardiac tissue.

14. The method of claim 13, wherein the cardiac function comprises normalized end diastolic volume, normalized end systolic volume, ejection fraction, or any combination thereof.

15. The method of claim 1, wherein the monomer is delivered epicardially.

16. The method of claim 1, wherein the monomer is delivered endocardially.

17. The method of claim 1, wherein the polymerization is effected by an initiator.

18. The method of claim 17, wherein the initiator comprises tetramethylethylenediamine.

19. The method of claim 1, wherein the reinforced region comprises an elastomer.

* * * * *

UNITED STATES PATENT AND TRADEMARK OFFICE
CERTIFICATE OF CORRECTION

PATENT NO.        : 9,486,404 B2                                    Page 1 of 1
APPLICATION NO.   : 13/430872
DATED             : November 8, 2016
INVENTOR(S)       : Jason A. Burdick et al.

It is certified that error appears in the above-identified patent and that said Letters Patent is hereby corrected as shown below:

In the Specification

Column 1,
Lines 15-18, delete "This invention was made with government support under grants HL63954, HL73021, and HL76560, awarded by the National Institutes of Health. The government has certain rights in this invention." and insert -- This invention was made with government support under grant number HL063954, HL073021 and HL076560 awarded by the National Institutes of Health. The government has certain rights in the invention. --

Signed and Sealed this
Twenty-fifth Day of April, 2017

Michelle K. Lee
*Director of the United States Patent and Trademark Office*